United States Patent
Yamazaki et al.

(10) Patent No.: US 11,898,139 B2
(45) Date of Patent: Feb. 13, 2024

(54) **CULTURING METHOD FOR GENUS *RHIZOBIUM* BACTERIA**

(71) Applicants: Kumiai Chemical Industry Co., Ltd., Taito-Ku (JP); K.I Chemical Industry Co., Ltd., Iwata (JP); Okayama Prefectural Government, Okayama (JP)

(72) Inventors: Toshinobu Yamazaki, Taito-Ku (JP); Shingo Hattori, Iwata (JP); Tatsuya Horiuchi, Iwata (JP)

(73) Assignees: Kumiai Chemical Industry Co., Ltd., Taito-Ku (JP); K.I Chemical Industry Co., Ltd., Iwata (JP); Okayama Prefectural Government, Okayama (JP)

( * ) Notice: Subject to any disclaimer, the term of this patent is extended or adjusted under 35 U.S.C. 154(b) by 224 days.

(21) Appl. No.: 16/758,950

(22) PCT Filed: Oct. 23, 2018

(86) PCT No.: PCT/JP2018/039397
§ 371 (c)(1),
(2) Date: Apr. 24, 2020

(87) PCT Pub. No.: WO2019/082906
PCT Pub. Date: May 2, 2019

(65) Prior Publication Data
US 2021/0180006 A1 Jun. 17, 2021

(30) Foreign Application Priority Data
Oct. 27, 2017 (JP) .................................. 2017-208572

(51) Int. Cl.
*C12N 1/20* (2006.01)
*C12N 1/04* (2006.01)

(52) U.S. Cl.
CPC .................. *C12N 1/20* (2013.01); *C12N 1/04* (2013.01); *C12N 2500/34* (2013.01); *C12N 2500/60* (2013.01)

(58) Field of Classification Search
CPC ........ C12N 1/20; C12N 1/04; C12N 2500/34; C12N 2500/60
See application file for complete search history.

(56) References Cited

U.S. PATENT DOCUMENTS 4,797,364 A    1/1989   Amen et al.

FOREIGN PATENT DOCUMENTS

| JP | 60-118182 A | 6/1985 |
|---|---|---|
| JP | 2009-201373 A | 9/2009 |
| JP | 2010-252680 A | 11/2010 |
| WO | WO 2012/067127 A1 | 5/2012 |

OTHER PUBLICATIONS

Kawaguchi, A. (2014). Reduction in pathogen populations at grapevine wound sites is associated with the mechanism underlying the biological control of crown gall by Rhizobium vitis strain ARK-1. Microbes and environments, ME14059 (Year: 2014).*
Yao, Li Juan, et al. "Rhizobium taibaishanense sp. nov., isolated from a root nodule of Kummerowia striata." International journal of systematic and evolutionary microbiology 62.2 (2012): 335-341 (Year: 2012).*
Bissonnette, N., Lalande, R., & Bordeleau, L. M. (1986). Large-scale production of Rhizobium meliloti on whey. Applied and environmental microbiology, 52(4), 838-841 (Year: 1986).*
Tan, Zhi-Yuan, et al. "Phylogenetic and genetic relationships of Mesorhizobium tianshanense and related rhizobia." International journal of systematic bacteriology 47.3 (1997): 874-879. (Year: 1997).*
Pereira, P. A. A., Oliver, A., Bliss, F. A., Crowe, L., & Crowe, J. (2002). Preservation of rhizobia by lyophilization with trehalose. Pesquisa Agropecuária Brasileira, 37, 831-839 (Year: 2002).*
Wei et al. "Rhizobium indigoferae sp. nov. and Sinorhizobium kummerowiae sp. nov., respectively isolated from Indigofera spp. and Kummerowia stipulacea." International Journal of Systematic and Evolutionary Microbiology 52.6 (2002): 2231-2239 (Year: 2002).*
Kawaguchi, A., K. Inoue, and Y. Ichinose. "Biological control of crown gall of grapevine, rose, and tomato by nonpathogenic Agrobacterium vitis strain VAR03-1." Phytopathology 98.11 (2008): 1218-1225 (Year: 2008).*
Andhare, P., et al (2017). Characterization and rheological behaviour analysis of the succinoglycan produced by Rhizobium radiobacter strain CAS from curd sample. Food Hydrocolloids, 64, 1-8 (Year: 2017).*
International Search Report dated Jan. 8, 2019 in PCT/JP2018/039397 filed Oct. 23, 2018, citing documents AA, AO-AR and AX therein, 2 pages.
McClure et al. "Construction of a Range of Derivatives of the Biological Control Strain *Agrobacterium rhizogenes* K84: a Study of Factors Involved in Biological Control of Crown Gall Disease," Applied and Environmental Microbiology, Oct. 1998, p. 3977-3982; 0099-2240898/$04.00+0; vol. 64, No. 10; Copyright @ 1998, American Society for Microbiology.

* cited by examiner

*Primary Examiner* — Robert J Yamasaki
*Assistant Examiner* — Trevor Kane
(74) *Attorney, Agent, or Firm* — Oblon, McClelland, Maier & Neustadt, L.L.P.

(57) ABSTRACT

Provided herein is a culturing method for bacteria of the genus *Rhizobium* whereby a low viscosity can be maintained in a culture solution during the culturing of and at the end of culturing of said bacteria, and that enables easy and efficient post-procedures, including concentration and separation of viable bacteria, among others. This is achieved by growing *Rhizobium* bacteria by liquid culture using a medium containing a disaccharide (for example, maltose, trehalose, lactose, sucrose) accounting for at least 25 mass % of the carbon source in the medium while maintaining a pH of 5.0 to 7.0 in the culture solution throughout the course of the culture, namely from the beginning of the culturing to the end of the culturing of said bacteria.

8 Claims, No Drawings

CULTURING METHOD FOR GENUS *RHIZOBIUM* BACTERIA

TECHNICAL FIELD

The present invention relates to a culturing method for bacteria of the genus *Rhizobium*, and the like. Specifically, the present invention relates to a culturing method for *Rhizobium* bacteria whereby a low viscosity is maintained in a culture solution during and after liquid culture of bacteria, and in which a medium composition and culture conditions are selected so as to increase the viable cell count and thus enable easy and efficient post-procedures, including concentration and separation of viable bacteria.

BACKGROUND ART

Crown gall disease is a plant disease caused by pathogenic soil bacteria *Rhizobium radiobacter* (other name: *Agrobacterium tumefaciens*), *Rhizobium rhizogenes* (other name: *Agrobacterium rhizogenes*), and *Rhizobium vitis* (other name: *Agrobacterium vitis*) (in the following, there are cases where these are referred to collectively as "crown gall bacteria"). Tumors called crown gall form on plants infected by these pathogens. The disease develop reducing plant vigor and, in severe cases, leading to decline and die. In Japan, crown gall disease is developed for the most part in fruits and flowers, thus damaging seriously to farming of fruits and flowers, and in managing of trees in places such as parks.

All of the crown gall-causing bacteria above have the Ti (tumor-inducing) plasmid, which induces tumors when the nuclear DNA of a plant cell is transformed with a part of the Ti-plasmid (T-DNA region). Once a tumor is formed, the tumor keeps growing even in the absence of crown gall bacteria, until it leads the plant to decline and die. Therefore, at present, it is difficult to cure the plants affected by crown gall. An important measure for control of crown gall disease, therefore, is to prevent a plant from being infected by crown gall bacteria.

Traditionally, such preventive measures against infection with crown gall bacteria have mostly been implemented by heat sterilization of the entire soil contaminated with crown gall bacteria, soil fumigation with a soil disinfectant such as a chloropicrin agent or a methyl bromide agent, or soil treatment with an antibiotic for Gram-negative bacteria (because of crown gall bacteria being Gram negative). A drawback, however, is that these methods result in creating poor soil by also sterilizing and removing useful soil bacteria in the soil, in addition to the crown gall bacteria. An organic fertilizer needs to be applied or other measures are needed to bring such poor soil back to soil conditions suited for intended plant growth. However, this requires a great deal of time, cost, and labor. The soil disinfectants used in fumigation are very toxic, and pose health risks to workers and people in the neighborhood.

As an alternative approach, prevention methods that use non-pathogenic bacteria as biopesticides have been proposed. Methods that are considered particularly effective are methods wherein use non-pathogenic *Rhizobium* bacteria as biopesticides. For example, PTL 1 discloses that non-pathogenic ARK-1, ARK-2, and ARK-3 strains of *Rhizobium vitis* show high crown-gall-disease control effect and high plant-seed-germination improving effect, and that microbial pesticides using these bacterial strains are promising for disease prevention.

However, a liquid culture of *Rhizobium* bacteria, particularly of the ARK-1, ARK-2, and ARK-3 strains, increases its viscosity when nutrients essential for bacterial growth are added in abundance during production culture and the like to improve bacterial growth. Such viscosity increase poses difficulty in stirring the culture, or in concentrating or separating viable bacteria after culture. For example, centrifugal concentration or separation of bacteria, when conducted to harvest viable cells under a constant centrifugal force, results in decreased sedimentation of bacteria with increase of viscosity, causing the bacteria to remain in supernatant. Increased numbers of viable bacteria being left unharvested mean increased cost of production.

Methods for lowering viscosity a culture solution, namely culture liquid of a microbial liquid culture are known, including, for example, a method that lowers viscosity of a culture solution by adding a 10 to 100 mM metal salt in producing polysaccharides through secretion from cells cultured in liquid medium (PTL 2), and a method that lowers viscosity of a culture solution by mutation treatment in bacteria of the genus *Aureobasidium* (PTL 3). However, the method described in PTL 2 is intended primarily for producing polysaccharides through secretion in liquid culture of plant cells, and is not suited for lowering viscosity of a *Rhizobium* liquid culture. In the mutation treatment method of PTL 3, it is unclear whether mutation in *Rhizobium* bacteria actually lowers viscosity of a culture solution, and the mutation involves the risk of altering the properties of bacterial strains such as bacterial growth and crown gall disease control effect. Indeed, at present, there is no report concerning lowering viscosity of a *Rhizobium* liquid culture.

Under these circumstances, there is a need in the industry for development of a technique for preventing viscosity increase in a culture solution during liquid-culturing and at the end of culturing *Rhizobium* bacteria.

PRIOR ART

Patent Literature

PTL 1: WO2012/067127
PTL 2: JP-A-H05-207888
PTL 3: JP-A-2007-319150

SUMMARY OF INVENTION

Technical Problem to be Solved by Invention

An object of the present invention is to provide a culture method for *Rhizobium* bacteria whereby a low viscosity can be maintained in a culture solution during liquid-culturing and at the end of culturing bacteria, and that enables easy and efficient post-procedures, including concentration and separation of viable bacteria, among others.

Means for Solving Problem

The present inventors conducted intensive studies to achieve the foregoing objects, and found that a low viscosity can be maintained in a culture solution throughout the culture of *Rhizobium* bacteria, namely from at the start, during and at the end of culturing said bacteria, while ensuring improvement of viable cell count when the medium used for the liquid culture of *Rhizobium* bacteria contains a disaccharide accounting for at least 25 mass % of the carbon source in the medium, and the pH of the *Rhizobium* culture solution is kept within a range of 5.0 to 7.0 throughout the course of the culture, and the present invention was completed.

Specifically, embodiments of the present invention are as follows.

(1) A culture method for bacteria of the genus *Rhizobium*, comprising growing a *Rhizobium* bacterium by liquid culture using a medium containing a disaccharide accounting for at least 25 mass % of a carbon source in the medium while maintaining a pH of 5.0 to 7.0 in a culture solution throughout the course of the culture, namely from the beginning of the culturing to the end the culturing.

(2) The method according to (1), wherein is disaccharide is one or two or more selected from maltose, trehalose, lactose, and sucrose.

(3) The method according to (1) or (2), wherein the *Rhizobium* bacterium is any one of *Rhizobium radiobacter*, *Rhizobium rhizogenes*, and *Rhizobium vitis*.

(4) The method according to any one of (1) to (3), wherein the *Rhizobium* bacterium is non-pathogenic.

(5) The method according to (1) or (2), wherein the *Rhizobium* bacterium is any one of *Rhizobium vitis* ARK-1 strain (FERM BP-11426), *Rhizobium vitis* ARK-2 strain (FERM BP-11427), *Rhizobium vitis* ARK-3 strain (FERM BP-11428), and *Agrobacterium radiobacter* K84 strain.

(6) The method according to any one of (1) to (5), wherein the liquid culture is a large scale culture, namely an at least 5-L mass culture.

(7) A method for producing viable *Rhizobium* bacteria, comprising:
  growing a *Rhizobium* bacterium by liquid culture using a medium containing a disaccharide containing at least 25 mass % of a carbon source in the medium while maintaining a pH of 5.0 to 7.0 in a culture solution throughout the course of the culture, namely from the beginning of the culturing to the end of the culturing; and
  concentrating and/or separating viable bacteria from the culture solution.

(8) The method according to (7), further comprising lyophilizing the viable bacteria.

(9) The method according to (7) or (8), wherein the disaccharide is one or two or more selected from maltose, trehalose, lactose, and sucrose.

(10) The method according to anyone of (7) to (9), wherein the *Rhizobium* bacterium is any one of *Rhizobium radiobacter*, *Rhizobium rhizogenes*, and *Rhizobium vitis*.

(11) The method according to any one of (7) to (10), wherein the *Rhizobium* bacterium is non-pathogenic.

(12) The method according to anyone of (7) to (9), wherein the *Rhizobium* bacterium is any one of *Rhizobium vitis* ARK-1 strain (FERM BP-11426), *Rhizobium vitis* ARK-2 strain (FERM BP-11427), *Rhizobium vitis* ARK-3 strain (FERM BP-11428), and *Agrobacterium radiobacter* K84 strain.

(13) The method according to any one of (7) to (12), wherein the liquid culture is a large scale culture, namely an at least 5-L mass culture.

(14) A culture of a bacterium of the genus *Rhizobium*, comprising the *Rhizobium* bacterium grown by liquid culture using a liquid medium containing a disaccharide accounting for at least 25 mass % of a carbon source in the medium while maintaining a pH of 5.0 to 7.0 in a culture solution throughout the course of the culture, namely from the beginning of the culturing to the end of the culturing.

(15) A culturing method for *Rhizobium vitis* ARK-1 strain (FERM BP-11426), *Rhizobium vitis* ARK-2 strain (FERM BP-11427), or *Rhizobium vitis* ARK-3 strain (FERM BP-11428), comprising growing the *Rhizobium* bacterium by liquid culture using a medium containing a disaccharide accounting for at least 25 mass % of a carbon source in the medium while maintaining a pH of 5.0 to 7.0 in a culture solution throughout the course of the culture, namely from the beginning of the culturing to the end of the culturing.

(16) A culturing method for *Agrobacterium radiobacter* K84 strain, comprising growing the *Rhizobium* bacterium by liquid culture using a medium containing a disaccharide accounting for at least 25 mass % of a carbon source in the medium while maintaining a pH of 5.0 to 6.0 in a culture solution throughout the course of the culture.

Advantageous Effects of Invention

With the present invention, a low viscosity can be maintained (viscosity increase is inhibited) in a culture solution throughout the culture of *Rhizobium* bacteria. This enables easy post-procedures, including concentration and separation of viable bacteria. By constantly adjusting pH during culture, it is possible to improve the viable cell count of *Rhizobium* after culture, in addition to inhibiting or lowering viscosity increase in the culture solution. This enables highly efficient production of viable bacteria in industry and in other applications. In consideration of production for industrial applications, the present invention is particularly effective for large scale culture using at least 5 L of a culture solution.

DESCRIPTION OF EMBODIMENTS

The present invention relates to a culture method for bacteria of the genus *Rhizobium*, among others. Examples of the *Rhizobium* bacteria of interest to the present invention include *Rhizobium alamii*, *Rhizobium alkalisoli*, *Rhizobium cellulosilyticum*, *Rhizobium daejeonense*, *Rhizobium endophyticum*, *Rhizobium etli*, *Rhizobium fabae*, *Rhizobium gallicum*, *Rhizobium giardinii*, *Rhizobium grahamii*, *Rhizobium hainanense*, *Rhizobium huautlense*, *Rhizobium galegae*, *Rhizobium indica*, *Rhizobium indicus*, *Rhizobium indigoferae*, *Rhizobium larrymoorei*, *Rhizobium leguminosarum*, *Rhizobium leucaenae*, *Rhizobium loessense*, *Rhizobium lupini*, *Rhizobium lusitanum*, *Rhizobium mesosinicum*, *Rhizobium miluonense*, *Rhizobium mongolense*, *Rhizobium multihospitium*, *Rhizobium nagarjuna nagarensis*, *Rhizobium oryzae*, *Rhizobium phaseoli*, *Rhizobium pisi*, *Rhizobium pusense*, *Rhizobium radiobacter*, *Rhizobium rhizogenes*, *Rhizobium rubi*, *Rhizobium selenitireducens*, *Rhizobium soli*, *Rhizobium Bullae*, *Rhizobium tibeticum*, *Rhizobium trifolii*, *Rhizobium tropici*, *Rhizobium tuxtlense*, *Rhizobium undicola*, *Rhizobium validum*, and *Rhizobium vitis*. Artificially modified strains of these bacteria (for example, through mutations or genetic recombination) are also of interest to the present invention.

Among the *Rhizobium* bacteria listed above, the present invention is suitably applicable to *Rhizobium radiobacter*, *Rhizobium rhizogenes*, and *Rhizobium vitis*. The culture methods and other aspects of the present invention are applicable to both crown gall bacteria and non-pathogenic *Rhizobium* bacteria. Particularly, it is preferable to apply the present invention to non-pathogenic *Rhizobium* bacteria such as the F2/5 (pT2TFXK) strain of *Rhizobium vitis* (other name: *Agrobacterium vitis*) (see the specification of U.S. Pat. No. 7,141,395), the ARK-1, ARK-2, and ARK-3 strains of *Rhizobium vitis*, and the K84 strain of *Rhizobium rhizogenes* (other name: *Agrobacterium radiobacter*; available from Nihon Nohyaku Co., Ltd. under the trade name Bacterose®). The present invention is also applicable to other naturally occurring non-pathogenic *Rhizobium* bacteria, as well as other non-pathogenic *Rhizobium* bacteria that have been artificially modified through, for example, mutations or genetic recombination. However, the present invention is particularly suited for the non-pathogenic ARK-1, ARK-2, and ARK-3 strains of *Rhizobium vitis*, and the non-pathogenic K84 strain of *Agrobacterium radiobacter*.

The non-pathogenic ARK-1, ARK-2, and ARK-3 strains of *Rhizobium* bacteria were first deposited at The National Institute of Advanced Industrial Science and Technology, Patent Organism Depositary (currently, The National Institute of Technology and Evaluation, Patent Organism Depositary) under these names on Oct. 14, 2010 (address: 2-5-8, Kazusa-Kamatari, Kisarazu, Chiba, 292-0818), and were later transferred to an international depositary authority (Oct. 31, 2011) with international deposition numbers FERM BP-11426, FERM BP-11427, and FERM BP-11428, respectively.

In the present invention, the *Rhizobium* bacteria are cultured and grown by liquid culture. For liquid culture, an inoculum of *Rhizobium* bacteria such as above is obtained first. The inoculum may be obtained by culturing the bacterial strains deposited in depositary authorities such as above, or culturing commercially available strains, using, for example, a plate medium. Alternatively, a skilled person will be able to isolate the desired inoculum from any of *Rhizobium* strains commonly occurring in nature. Foreign strains, and strains that have been mutated in a closed environment are also available from biological resource institutions such as the NITE, abbreviation of The National Institute of Technology and Evaluation, Biotechnology Center (NRBC), provided that the strains are known strains. For inoculation, it is also possible to use non-naturally occurring bacterial strains, for example, such as bacterial strains artificially produced by genetic recombination, which may be strains produced in a laboratory or strains provided by an external source, or may be pure cultures of these strains.

Preferably, the inoculum is precultured (expansion culture) with a small quantity of medium, prior to main culture, in order to moderately increase the number of cells. Because the preculture is small scale, it is not particularly bound to conditions such as the carbon source and culture pH, and may be carried out by appropriately using a known medium and known culture conditions used for preculture of *Rhizobium* bacteria.

This is followed by the main, liquid culture of the *Rhizobium* bacteria. The carbon source used for the medium in main culture contains a disaccharide accounting for at least 25 mass %, preferably at least 40 mass %, more preferably at least 55 mass %, most preferably at least 70 mass % of the carbon source in the medium. Examples of the disaccharide include sucrose, lactulose, lactose, maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, vicianose, xylobiose, and primeverose. Preferably, the disaccharide is one or two or more selected from maltose, trehalose, sucrose, and lactose. However, the disaccharide is not limited to these.

Aside from disaccharides, the medium may additionally contain components that are usable for liquid culture of *Rhizobium* bacteria. Examples of such components include a carbon source, a nitrogen source, inorganic salts and the like generally used in microbial liquid culture. Examples of the carbon source include sugars such as starch and molasses, and organic acids such as citric acid (used in amounts that do not disturb the proportion of disaccharide thereto). Examples of the nitrogen source include organic nitrogen sources such as yeast extracts, soybean peptides, meat extracts, and peptone, and inorganic nitrogen sources such as ammonia, ammonium salts (e.g., ammonium sulfate, ammonium phosphate, and ammonium chloride), and nitrates. Examples of the mineral salts include salts of phosphoric acid, potassium, magnesium, manganese, and sodium. The medium also may be supplemented with trace amounts of organic nutrients, such as vitamins. It is also possible to use a defoaming agent, which may be any defoaming agent (for example, a silicone-base defoaming agent, a polyether-base defoaming agent), provided that it exhibits a defoaming effect without causing adverse effects on *Rhizobium* bacterial growth.

The *Rhizobium* bacteria are grown by liquid culture using such media. Main culture may be carried out under aerobic conditions, using, for example, aerated agitation or shaking culture, or fed-batch culture. The culture temperature conditions and culture time are not particularly limited. The culture temperature is selected from about 10 to 40° C., preferably about 15 to 35° C. The standard culture time is about 24 to 72 hours.

In main culture, the pH of the culture solution is kept (maintained) at 5.0 to 7.0, more preferably 5.5 to 7.0 throughout the culture. For example, in the case of the ARK-1, ARK-2, or ARK-3 strain, the pH of the culture solution is kept (maintained) at preferably 5.0 to 7.0, more preferably 5.5 to 7.0, most preferably 6.0 to 7.0. For the K84 strain, the pH of the culture solution is kept (maintained) at preferably 5.0 to 7.0, more preferably 5.0 to 6.5, most preferably 5.0 to 6.0. In this way, it is possible to improve the viable cell count of *Rhizobium* after culture, in addition to inhibiting viscosity increase in the culture solution. The method of keeping the pH is not particularly limited. However, because a liquid culture of *Rhizobium* bacteria typically shows gradual pH increase as the culture progresses, it is preferable to use a method that inhibits pH increase with the use of an acid such as phosphoric acid or sulfuric acid. The pH can be increased by using a base such as sodium hydroxide or ammonia, if so desired. Alternatively, for example, a method may be used that takes advantage of the buffering effect of a weak acid and a salt thereof, or a weak base and a salt thereof (e.g., a combination of acetic acid and sodium acetate, or a combination of dipotassium hydrogenphosphate and potassium dihydrogenphosphate) by appropriately mixing such substances into the medium in advance, or by appropriately adding these to the medium being cultured.

All procedures in the culture are aseptically performed, and the medium components and the materials used for pH adjustment are sterilized before use. Typically, sterilization may be achieved by steam sterilization using an autoclave. However, appropriately selected alternative means may be used for materials that cannot withstand high temperature and high pressure. Non-limiting examples of sterilization methods other than steam sterilization include heat sterilization such as direct flame sterilization and dry heat sterilization; electromagnetic sterilization that applies ionizing radiation such as y rays, X-rays, and ultraviolet rays (UV-C) of 200 to 280 nm wavelengths, or non-ionizing radiation such as microwaves and high-frequency waves; gas sterilization using, for example, ethylene oxide gas; chemical sterilization that makes use of chemical actions, such as ethanol sterilization, hydrogen peroxide low-temperature plasma sterilization, and sterilization using, for example, glutaraldehyde, phthaldialdehyde, hypochlorous acid, and peracetic acid; and sterilization by means of separation and removal, such as filtration.

The resulting culture solution of Rhizobium bacteria may be directly used in the form of a microbial pesticide or active pesticidal ingredients. However, this requires a large quantity of culture solution for actual use. For considerations such as delivery and preservation, the cost can be reduced when the culture solution is prepared into a more concentrated and compact form by, for example, concentrating the viable bacteria, and/or formulating the viable bacteria into a preparation. The viable bacteria can be concentrated by using an ordinary method, for example, such as centrifugation and membrane concentration. In the present invention, concentration can be achieved very easily and efficiently because of the low viscosity at the end of liquid culture. Examples of the formulation method include lyophilization, fluidized bed drying, and spray drying. Preferably, the liquid culture is formulated into a lyophilized composition. In the case of formulation by methods such as drying, it is preferable to add a protecting agent (e.g., proteins and hydrolysates thereof, carbohydrates, sugar alcohols, amino acids and salts thereof, and ionic halide salts) to the culture solution at the end of culture or to the concentrate.

The effect of the present invention becomes particularly prominent in mass culture (mass liquid culture) using at least 5 L of a culture solution, such as in industrial production. In mass culture, viscosity increase in a culture solution often leads to insufficient stirring and aeration, and usually poses considerable difficulty in the concentration process performed after culture. However, the present invention is also effective for such mass culture.

The cultured viable Rhizobium bacteria, and preparations and other products derived from the cultured viable bacteria can be used as biopesticides for applications such as crown gall disease control, with the provision that the grown bacteria are ensured to be non-pathogenic. For example, the biopesticide can be used to control crown gall and other diseases in agricultural and horticultural crops by being applied to plants (including the seeds) or soil (for example, by spraying to a soil surface, soil injection, dipping a plant in bacterial solution, or dust coating of a plant with a bacterial powder).

The types of plants to which the biopesticide is applicable are not particularly limited. Specific examples include Rosaceae plants such as apple, rose, Japanese plum, and cherry; Asteraceae plants such as *Chrysanthemum morifolium*; Vitaceae plants such as grape; and Solanaceae plants such as tomato. The ARK-1 and ARK-3 strains exhibit a high crown gall disease control effect for all of these plants. The ARK-2 strain exhibits a crown gall disease control effect particularly for roses, grapes, and tomatoes. The K84 strain exhibits a crown gall disease control effect particularly for apples, roses, and *chrysanthemum*, for example *Chrysanthemum morifolium*.

By culturing Rhizobium bacteria by liquid culture using a medium containing a disaccharide accounting for at least 25 mass % of the carbon source in the medium while maintaining a pH of 5.0 to 7.0 in the liquid culture throughout the course of the culture, namely from the beginning of the culturing to the end of the culturing, a low viscosity can be maintained (viscosity increase is inhibited) in the culture solution during culturing and at the end of culturing of Rhizobium bacteria. This enables easy and efficient concentration and separation of viable bacteria in a later step, and in addition to increasing the number of viable bacteria, enabling highly efficient production in industry and in other applications.

As used herein, "carbon source" means any of compounds (mostly sugars and organic acids) containing carbon, hydrogen, and oxygen, and that can be utilized by Rhizobium bacteria during liquid culture.

EXAMPLES

Examples of the present invention are described below. It is to be noted that the present invention is not limited to the Examples below, and various modifications are possible within the technical idea of the present invention. In the following Examples, all procedures were aseptically performed. In the following, "part(s)" means part(s) by mass.

Preparation of NA (Nutrient Agar) Plate Medium

For preparation of NA plate medium, 5 parts of meat extract, 10 parts of peptone, 5 parts of sodium chloride, 15 parts of agar, and 1,000 parts of water were mixed, and heated to completely dissolve. The mixture was poured into a Petri dish, and cooled to prepare an NA plate medium.

Preparation of Preculture Medium

For preparation of preculture medium, 17 parts of soybean peptide, 3 parts of yeast extract, 2.5 parts of glucose, 5 parts of sodium chloride, and 1,000 parts of water were mixed.

Test Example 1

A glycerol stock of *Rhizobium vitis* ARK-1 strain was thawed, and inoculated to the NA medium by streaking. The cells were statically cultured in a 28° C. constant-temperature room for 1 day to prepare an inoculum. For preculture, one platinum loop of the inoculum was transferred to inoculate the preculture medium. Preculture was carried out for 1 day in a 28° C. constant-temperature room using a rotary shaker (190 rpm). A control medium was prepared by mixing main culture medium components including 102 parts of soybean peptide, 18 parts of yeast extract, 30 parts of sodium chloride, 30 parts of Disfoam® NQH-7403 (defoaming agent), and 6,000 parts of water. Separately, said medium was supplemented with 120 parts of maltose, glucose, fructose, mannitol, trehalose, lactose, sucrose, or starch as a carbon source to prepare respectively 8 kinds of media containing above carbon component. For main culture, the preculture was inoculated to 6 L of the control medium and to each of the eight media containing carbon component (6 L each). The main culture was carried out at 28° C. for 2 days using a 10-L jar fermenter. The cells were cultured under the controlled pH of 7 or less (in a pH range of about 6.5 to 7.0) by maintaining a culture solution pH of 7 or below with phosphoric acid throughout the course of main culture.

The viscosity (mPa·s) of the culture solution, and the number of viable bacteria (cfu/ml) at the end of culture were measured using ordinary methods. The results are presented in the Table 1 below.

TABLE 1

| Carbon source | Viable cell count (cfu/ml) | Viscosity of culture solution (mPa · s) |
|---|---|---|
| Control | $1.1 \times 10^{10}$ | 13 |
| Maltose | $3.2 \times 10^{10}$ | 28 |
| Glucose | $1.9 \times 10^{10}$ | 632 |

TABLE 1-continued

| Carbon source | Viable cell count (cfu/ml) | Viscosity of culture solution (mPa · s) |
|---|---|---|
| Fructose | $1.9 \times 10^{10}$ | 563 |
| Mannitol | $3.1 \times 10^{10}$ | 1885 |
| Trehalose | $4.0 \times 10^{10}$ | 42 |
| Lactose | $3.1 \times 10^{10}$ | 20 |
| Sucrose | $3.4 \times 10^{10}$ | 176 |
| Starch | $1.1 \times 10^{10}$ | 12 |

As can be seen from these results, the culture solutions had notably high viscosities when glucose, fructose, and mannitol were used as carbon source. The viscosity was low in the culture solution that contained starch as carbon source. The same levels of viscosity and viable cell count observed in the control and in the culture solution supplemented with starch are probably due to the ARK-1 strain being unable to utilize starch. In contrast, the culture solutions containing maltose, trehalose, lactose, and sucrose as carbon source had low viscosities, and contained sufficiently large numbers of viable cells after culture. The results confirmed that viscosity increase in a culture solution of the ARK-1 strain can be inhibited, and the viable cell count improves when disaccharides are used as carbon source and the pH is adjusted during the culture.

A similar test was conducted by preparing an inoculum and carrying out the preculture in the same manner. For the test, a medium was prepared by mixing main culture medium components including 102 parts of soybean peptide, 18 parts of yeast extract, 30 parts of sodium chloride, 30 parts of Disfoam® NQH-7403, and 6,000 parts of water. Said medium was then supplemented with 120 parts of maltose, trehalose, lactose, or sucrose as a carbon source to prepare respectively 4 kinds of media containing above carbon source. For main culture, the four media (6 L each) were each inoculated with the preculture. Main culture was carried out at 28° C. for 2 days using a 10-L jar fermenter. The pH of the culture solution was not controlled during the culture.

The pH and viscosity of the culture solution, and the number of viable cells at the end of culture were measured using ordinary methods. The results are presented in the Table 2 below.

TABLE 2

| Carbon source | Viable cell count (cfu/ml) | Viscosity of culture solution (mPa · s) | pH at the end of culture |
|---|---|---|---|
| Maltose | $2.5 \times 10^{10}$ | 150 | 8.1 |
| Trehalose | $1.3 \times 10^{10}$ | 144 | 8.0 |
| Lactose | $1.8 \times 10^{10}$ | 32 | 8.4 |
| Sucrose | $2.6 \times 10^{10}$ | 424 | 8.2 |

As can be seen from the results, the viscosity showed slight increases compared to when the same disaccharides were used as carbon source with pH adjustment, though the extent of increase was not as large as when sugars other than disaccharides were used as carbon source, such as when using glucose. The viable cell count was also slightly smaller in case of no pH adjustment. These results therefore confirmed that use of disaccharides as carbon source, and the pH adjustment during culture are highly effective for inhibiting viscosity increase in a culture solution of the ARK-1 strain, and for improving the viable cell count of the ARK-1 strain.

Test Example 2

Glycerol stocks of the *Rhizobium vitis* ARK-2 strain, the *Rhizobium vitis* ARK-3 strain, and the *Agrobacterium radiobacter* K84 strain were thawed, and inoculated to the NA medium by streaking. The cells were statically cultured in a 28° C. constant-temperature room for 1 day to prepare an inoculum. For preculture, one plutinum loop of the inoculum was then transferred to inoculate the preculture medium. Preculture was carried out in a 28° C. constant-temperature room for 1 day using a rotary shaker (190 rpm). A control medium was prepared by mixing main culture medium components including 102 parts of soybean peptide, 18 parts of yeast extract, 30 parts of sodium chloride, 30 parts of Disfoam® NQH-7403 (defoaming agent), and 6,000 parts of water. Separately, said medium was supplemented with 120 parts of maltose, glucose, or mannitol as a carbon source to prepare respectively 3 kinds of media containing above carbon component. For main culture, the preculture was inoculated to 6 L of the control medium and to each of the three media containing carbon component (6 L each) The main culture was carried out at 28° C. for 2 days using a 10-L jar fermenter. For the *Rhizobium vitis* ARK-2 and ARK-3 strains, the cells were cultured under the controlled pH of 7 or less by maintaining a culture solution pH of 7 or below with phosphoric acid throughout the course of main culture. For the *Agrobacterium radiobacter* K84 strain, the cells were cultured under the controlled pH of 6 or less by maintaining a culture solution pH of 6 or below with phosphoric acid throughout the course of main culture. For the culture of *Agrobacterium radiobacter* K84 strain supplemented with glucose as carbon source, the cells were cultured under the controlled pH of 5.0 or more with ammonia water.

The viscosity (mPa·s) of the culture solution, and the number of viable cells (cfu/ml) at the end of culture were measured using ordinary methods. The results are presented in the Table 3 below.

TABLE 3

| | ARK-2 strain | | ARK-3 strain | | K-84 strain | |
|---|---|---|---|---|---|---|
| Carbon source | Viable cell count (cfu/ml) | Viscosity of culture solution (mPa · s) | Viable cell count (cfu/ml) | Viscosity of culture solution (mPa · s) | Viable cell count (cfu/ml) | Viscosity of culture solution (mPa · s) |
| Control | $1.3 \times 10^{10}$ | 20 | $1.3 \times 10^{10}$ | 15 | $8.7 \times 10^{9}$ | 10 |
| Maltose | $4.4 \times 10^{10}$ | 29 | $3.2 \times 10^{10}$ | 28 | $3.7 \times 10^{10}$ | 15 |
| Glucose | $3.5 \times 10^{10}$ | 707 | $1.9 \times 10^{10}$ | 363 | $2.3 \times 10^{10}$ | 45 |
| Mannitol | $3.1 \times 10^{10}$ | 426 | $2.2 \times 10^{10}$ | 890 | $2.9 \times 10^{10}$ | 115 |

The culture solution had low viscosity and sufficiently large numbers of viable cells when disaccharide maltose was added as carbon source, as compared to when monosaccharide glucose and sugar alcohol mannitol were added. In liquid cultures of *Rhizobium vitis* ARK-2 strain, *Rhizobium vitis* ARK-3 strain, and *Agrobacterium radiobacter* K84 strain, viscosity increase was inhibited, and the viable cell count improved when a disaccharide was used as carbon source and the pH was adjusted during the culture, as with the case of the *Rhizobium vitis* ARK-1 strain.

Test Example 3

A similar test was conducted by preparing an inoculum and carrying out the preculture in the same manner as in Test Example 1. For the test, a medium was prepared by mixing main culture medium components including 306 parts of soybean peptide, 54 parts of yeast extract, 90 parts of sodium chloride; 360 parts of maltose, 90 parts of Disfoam® NQH-7403, and 18,000 parts of water. For main culture, the preculture was inoculated to 18 L of said medium. Main culture was carried out at 28° C. for 2 days using a 30-L jar fermenter. In main culture, the culture solution was divided into nine pH groups with the upper limit pH of 4.0, 4.5, 5.0, 5.5, 6.0, 6.5, 7.0, 7.5, and 8.0. For each group, the cells were cultured under a controlled pH by maintaining a culture solution pH that does not exceed the set pH value (within the pH range of −0.5 and less of the set pH), using phosphoric acid. As a control, the cells were also cultured without controlling the pH of the culture solution.

The pH and viscosity of the culture solution, and the number of viable cells at the end of culture were measured using ordinary methods. The results are presented in the Table 4 below.

TABLE 4

| Controlled pH (upper limit) | Viable cell count (cfu/ml) | Viscosity of culture solution (mPa · s) |
| --- | --- | --- |
| Control | $2.4 \times 10^{10}$ | 185 |
| 4.0 | $1.0 \times 10^{7}$ or less | 4 |
| 4.5 | $1.9 \times 10^{8}$ | 4 |
| 5.0 | $2.0 \times 10^{10}$ | 24 |
| 5.5 | $3.4 \times 10^{10}$ | 27 |
| 6.0 | $3.0 \times 10^{10}$ | 24 |
| 6.5 | $3.4 \times 10^{10}$ | 34 |
| 7.0 | $3.3 \times 10^{10}$ | 37 |
| 7.5 | $2.4 \times 10^{10}$ | 182 |
| 8.0 | $2.3 \times 10^{10}$ | 190 |

The control had a pH of 8.3 at the end of culture. As shown in Table 4, the culture solution had a slightly high viscosity at a pH of 7.5 or higher, and the growth was poor in a pH of 4.5 or less. In contrast, the culture solution had low viscosity in a pH range of 5.0 to 7.0, and the viable cell count was shown to greatly improve in this pH range, particularly at pH 5.5 to 7.0.

Test Example 4

A similar test was conducted by preparing an inoculum and carrying out the preculture in the same manner as in Test Example 1, except that the *Rhizobium vitis* ARK-2 strain, the *Rhizobium vitis* ARK-3 strain, and the *Agrobacterium radiobacter* K84 strain were used in addition to the ARK-1 strain. For the test, a medium was prepared by mixing main culture medium components including 102 parts of soybean peptide, 18 parts of yeast extract, 30 parts of sodium chloride, 120 parts of maltose, 30 parts of Disfoam® NQH-7403, and 6,000 parts of water. For main culture, the preculture was inoculated to 6 L of said medium. Main culture was carried out at 28° C. for 2 days using a 10 L jar fermenter, with and without the pH control to maintain a culture solution pH of 7.0 or below with phosphoric acid. The viscosity of the culture solution, and the number of viable cells at the end of culture were measured using ordinary methods. The results are presented in the Table 5 below.

TABLE 5

| | Example: with pH control | | Comparative Example: without pH control | |
| --- | --- | --- | --- | --- |
| Strain | Viable cell count (cfu/ml) | Viscosity of culture solution (mPa · s) | Viable cell count (cfu/ml) | Viscosity of culture solution (mPa · s) |
| ARK-1 | $3.3 \times 10^{10}$ | 37 | $2.4 \times 10^{10}$ | 185 |
| ARK-2 | $3.2 \times 10^{10}$ | 40 | $2.6 \times 10^{10}$ | 94 |
| ARK-3 | $3.6 \times 10^{10}$ | 44 | $2.2 \times 10^{10}$ | 170 |
| K84 | $2.9 \times 10^{10}$ | 345 | $2.2 \times 10^{10}$ | 393 |

These results confirmed that control of culture solution pH during main culture was shown to be highly effective for improving viable cell count and lowering culture solution viscosity in the ARK-2 and ARK-3 strains, as with the case of the ARK-1 strain. In the K84 strain, control of culture solution pH during main culture was also shown to be effective for improving viable cell count and lowering culture solution viscosity, though the effect was slightly weaker than that observed for the ARK-1, ARK-2, and ARK-3 strains.

Test Example 5

A similar test was conducted by preparing an inoculum and carrying out the preculture in the same manner as in Test Example 2, except that the *Rhizobium vitis* ARK-2 strain, the *Rhizobium vitis* ARK-3 strain, and the *Agrobacterium radiobacter* K84 strain were used in addition to the ARK-1 strain. For the test, a medium was prepared by mixing main culture medium components including 102 parts of soybean peptide, 18 parts of yeast extract, 30 parts of sodium chloride, 120 parts of maltose, 30 parts of Disfoam® NQH-7403, and 6,000 parts of water. For main culture, the preculture was inoculated to 6 L of the medium. Main culture was carried out at 28° C. for 2 days using a 10 L jar fermenter, with and without the pH control to maintain a culture solution pH of 6.0 or below with phosphoric acid. The viscosity of the culture solution, and the number of viable cells at the end of culture were measured using ordinary methods. The results are presented in the Table 6 below.

TABLE 6

| | Example: with pH control | | Comparative Example: without pH control | |
| --- | --- | --- | --- | --- |
| Strain | Viable cell count (cfu/ml) | Viscosity of culture solution (mPa · s) | Viable cell count (cfu/ml) | Viscosity of culture solution (mPa · s) |
| ARK-1 | $3.0 \times 10^{10}$ | 24 | $2.4 \times 10^{10}$ | 185 |
| ARK-2 | $3.5 \times 10^{10}$ | 17 | $2.6 \times 10^{10}$ | 94 |

TABLE 6-continued

| | Example: with pH control | | Comparative Example: without pH control | |
|---|---|---|---|---|
| Strain | Viable cell count (cfu/ml) | Viscosity of culture solution (mPa · s) | Viable cell count (cfu/ml) | Viscosity of culture solution (mPa · s) |
| ARK-3 | $3.1 \times 10^{10}$ | 21 | $2.2 \times 10^{10}$ | 170 |
| K84 | $3.3 \times 10^{10}$ | 28 | $2.2 \times 10^{10}$ | 393 |

These results confirmed that control of culture solution pH during main culture was shown to be highly effective for inhibiting culture solution viscosity increase and improving viable cell count in the *Rhizobium vitis* ARK-1, ARK-2, and ARK-3 strains and the *Agrobacterium radiobacter* K84 strain.

Test Example 6

A similar test was conducted by preparing an inoculum and carrying out the preculture in the same manner as in Test Example 2, except for using *Rhizobium vitis* ARK-1 strain. For the test, a medium was prepared by mixing main culture medium components including 306 parts of soybean peptide, 54 parts of yeast extract, 90 parts of sodium chloride, 360 parts of maltose, 90 parts of Disfoam® NQH-7403, and 18,000 parts of water, For main culture, the preculture was inoculated to 18 L of said medium. Main culture was carried out at 28° C. for 2 days using a 30-L jar fermenter. In main culture, the culture solution was divided into seven pH groups with the upper limit pH of 5.0, 5.5, 6.0, 6.5, 7.0, 7.5, and 8.0. For each group, the cells were cultured under a controlled pH by maintaining a culture solution pH that does not exceed the set pH value (within the pH range of −0.5 and less of the set pH), using phosphoric acid. As a control, the cells were also cultured without controlling the pH of the culture solution. After main culture, the culture solution was centrifuged, and a bacteria concentrate was obtained by discarding the supernatant. In order to prepare an aqueous solution of a protecting agent for lyophilization, 20 parts of trehalose, 10 parts of sodium glutamate, 8 parts of cysteine hydrochloride, 1 part of sodium carboxymethyl cellulose, and 61 parts of water were mixed, and the pH was adjusted to 7 with a minute quantity of sodium hydroxide aqueous solution. After mixing 50 parts of the bacteria concentrate with 50 parts of the aqueous solution of a protecting agent for lyophilization, a sodium hydroxide aqueous solution was dropped to bring the pH to 7 again and obtain a liquid concentrate of viable bacteria. From the liquid concentrate of viable bacteria, 7.0 g was transferred to a 10-mL vial, and pre-frozen with a deep freezer set at −80° C. The cells were then lyophilized for 48 hours under a reduced pressure of about 200 m Torr created by a lyophilizer (VirTis 25 L Genesis SQ Super ES-55, available from SP Industries, Inc.) to obtain a lyophilized composition. The lyophilized composition in the vial had a total mass of 2.0 g with a moisture content of 7.9 mass %. After sealing the vial, the lyophilized composition was statically stored in a 6° C. refrigerator or in a 28° C. constant-temperature room.

Evaluation of Viable Cell Viability Immediately after Lyophilization

The viable cell concentration (cfu/g) of the *Rhizobium vitis* ARK-1 strain in the lyophilized composition of Test Example 6 was measured using an ordinary method, and the measured value was multiplied by the total mass (g) of the lyophilized composition to determine the total viable cell count (cfu) of the *Rhizobium vitis* ARK-1 strain in the lyophilized composition. For calculation of the viable cell viability (%) of *Rhizobium vitis* ARK-1 strain immediately after lyophilization, the measured total viable cell count was divided by the total viable cell count of *Rhizobium vitis* ARK-1 strain in 7 g of the liquid concentrate of viable bacteria.

Evaluation of Viable Cell Viability for Preservation Stability

The viable cell concentration (cfu/g) of the *Rhizobium vitis* ARK-1 strain in the lyophilized composition was measured at different time points (days) during preservation, using an ordinary method. The measured value was multiplied by the total mass (g) of the lyophilized composition to determine the total viable cell count (cfu) of the *Rhizobium vitis* ARK-1 strain in the lyophilized composition. The measured total viable cell count was divided by the total viable cell count immediately after lyophilization to calculate the viable cell viability (%) of *Rhizobium vitis* ARK-1 strain at different time points (days) during preservation.

Table 7 shows the total viable cell count per vial before lyophilization of the liquid concentrate of viable bacteria from culture solutions prepared under controlled pH.

TABLE 7

| Controlled pH (upper limit) | Total mass (g) | Viable cell concentration (cfu/g) | Total viable cell count (cfu) |
|---|---|---|---|
| Control | 7.0 | $3.6 \times 10^{11}$ | $2.5 \times 10^{12}$ |
| 6.0 | 7.0 | $3.6 \times 10^{11}$ | $2.5 \times 10^{12}$ |
| 6.5 | 7.0 | $3.3 \times 10^{11}$ | $2.3 \times 10^{12}$ |
| 7.0 | 7.0 | $3.5 \times 10^{11}$ | $2.5 \times 10^{12}$ |
| 7.5 | 7.0 | $3.1 \times 10^{11}$ | $2.2 \times 10^{12}$ |
| 8.0 | 7.0 | $3.4 \times 10^{11}$ | $2.4 \times 10^{12}$ |

Table 8 shows the viable cell viability (%) immediately after lyophilization of the lyophilized composition from culture solutions prepared under controlled pH.

TABLE 8

| Controlled pH (upper limit) | Moisture content (%) | Total mass (g) | Viable cell concentration (cfu/g) | Total viable cell count (cfu) | Viability of viable cells (%) |
|---|---|---|---|---|---|
| Control | 7.9 | 2.0 | $5.6 \times 10^{11}$ | $1.1 \times 10^{12}$ | 44 |
| 6.0 | 7.9 | 2.0 | $6.1 \times 10^{11}$ | $1.2 \times 10^{12}$ | 48 |
| 6.5 | 7.9 | 2.0 | $6.6 \times 10^{11}$ | $1.3 \times 10^{12}$ | 57 |
| 7.0 | 7.9 | 2.0 | $7.1 \times 10^{11}$ | $1.4 \times 10^{12}$ | 56 |
| 7.5 | 7.9 | 2.0 | $6.0 \times 10^{11}$ | $1.2 \times 10^{12}$ | 55 |
| 8.0 | 7.9 | 2.0 | $6.1 \times 10^{11}$ | $1.2 \times 10^{12}$ | 50 |

Table 9 shows the preservation stability at 6° C. for lyophilized compositions from culture solutions prepared under controlled pH.

TABLE 9

| Controlled pH (upper limit) | | Preservation time at 6° C. in days | | | | |
| --- | --- | --- | --- | --- | --- | --- |
| | | Day 0 | Day 10 | Day 20 | Day 30 | Day 65 |
| Control | Total viable cell count (cfu) | $1.1 \times 10^{12}$ | $5.0 \times 10^{11}$ | $4.2 \times 10^{11}$ | $2.6 \times 10^{11}$ | $9.0 \times 10^{10}$ |
| | Viability of viable cells (%) | 100 | 45 | 38 | 24 | 8 |
| 6.0 | Total viable cell count (cfu) | $1.2 \times 10^{12}$ | $1.2 \times 10^{12}$ | $1.2 \times 10^{12}$ | $1.1 \times 10^{12}$ | $9.6 \times 10^{11}$ |
| | Viability of viable cells (%) | 100 | 100 | 100 | 92 | 80 |
| 6.5 | Total viable cell count (cfu) | $1.3 \times 10^{12}$ | $1.2 \times 10^{12}$ | $1.5 \times 10^{12}$ | $1.3 \times 10^{12}$ | $1.3 \times 10^{12}$ |
| | Viability of viable cells (%) | 100 | 92 | 115 | 100 | 100 |
| 7.0 | Total viable cell count (cfu) | $1.4 \times 10^{12}$ | $1.4 \times 10^{12}$ | $1.6 \times 10^{12}$ | $1.4 \times 10^{12}$ | $1.2 \times 10^{12}$ |
| | Viability of viable cells (%) | 100 | 100 | 114 | 100 | 86 |
| 7.5 | Total viable cell count (cfu) | $1.2 \times 10^{12}$ | $4.4 \times 10^{11}$ | $3.0 \times 10^{11}$ | $2.6 \times 10^{11}$ | $1.3 \times 10^{11}$ |
| | Viability of viable cells (%) | 100 | 37 | 25 | 22 | 11 |
| 8.0 | Total viable cell count (cfu) | $1.2 \times 10^{12}$ | $4.8 \times 10^{11}$ | $3.0 \times 10^{11}$ | $5.4 \times 10^{11}$ | $2.0 \times 10^{11}$ |
| | Viability of viable cells (%) | 100 | 40 | 25 | 45 | 17 |

Table 10 shows the preservation stability at 28° C. for lyophilized compositions from culture solutions prepared under controlled pH.

TABLE 10

| Lyophilized composition | | Preservation time at 28° C. in days | | | | |
| --- | --- | --- | --- | --- | --- | --- |
| Controlled pH (upper limit) | | Day 0 | Day 10 | Day 20 | Day 30 | Day 65 |
| Control | Total viable cell count (cfu) | $1.1 \times 10^{12}$ | $1.8 \times 10^{11}$ | $4.0 \times 10^{11}$ | $1.2 \times 10^{11}$ | $6.2 \times 10^{10}$ |
| | Viability of viable cells (%) | 100 | 16 | 36 | 11 | 6 |
| 6.0 | Total viable cell count (cfu) | $1.2 \times 10^{12}$ | $9.2 \times 10^{11}$ | $6.2 \times 10^{11}$ | $4.4 \times 10^{11}$ | $4.4 \times 10^{11}$ |
| | Viability of viable cells (%) | 100 | 77 | 52 | 37 | 37 |
| 6.5 | Total viable cell count (cfu) | $1.3 \times 10^{12}$ | $8.8 \times 10^{11}$ | $9.8 \times 10^{11}$ | $9.4 \times 10^{11}$ | $7.0 \times 10^{11}$ |
| | Viability of viable cells (%) | 100 | 68 | 75 | 72 | 54 |
| 7.0 | Total viable cell count (cfu) | $1.4 \times 10^{12}$ | $8.6 \times 10^{11}$ | $9.2 \times 10^{11}$ | $9.4 \times 10^{11}$ | $6.2 \times 10^{11}$ |
| | Viability of viable cells (%) | 100 | 61 | 66 | 67 | 44 |
| 7.5 | Total viable cell count (cfu) | $1.2 \times 10^{12}$ | $1.3 \times 10^{11}$ | $2.0 \times 10^{11}$ | $4.4 \times 10^{10}$ | $7.0 \times 10^{10}$ |
| | Viability of viable cells (%) | 100 | 11 | 17 | 4 | 6 |
| 8.0 | Total viable cell count (cfu) | $1.2 \times 10^{12}$ | $2.4 \times 10^{11}$ | $2.0 \times 10^{11}$ | $5.4 \times 10^{10}$ | $7.6 \times 10^{10}$ |
| | Viability of viable cells (%) | 100 | 20 | 17 | 5 | 6 |

As can be seen from Table 8, the viable cell viability measured immediately after lyophilization in the presence of pH control of the main culture was not significantly different from that without pH control. As shown in Tables 9 and 10, the preservation stability was low at a pH of 7.5 and higher. However, in case of culture under the controlled pH range of 6.0 to 7.0 or below, the lyophilized composition had high preservation stability under both 6° C. and 28° C. storage conditions. The pH control to maintain a pH of 7.0 or below during main culture was therefore shown to be highly effective not only for inhibiting viscosity increase in a culture solution and improving the viable cell count, but for improving the preservation stability of the lyophilized composition.

The present invention can be summarized as follows.

An objective of the present invention is to provide a liquid-culturing method for *Rhizobium* bacteria whereby a low viscosity can be maintained in a culture solution during liquid-culturing of and at the end of culturing of said bacteria, and that enables easy and efficient post-procedures, including concentration and separation of viable bacteria, among others.

The foregoing objective is achieved by growing *Rhizobium* bacteria by liquid culture using a medium containing a disaccharide (for example, maltose, trehalose, lactose, sucrose) accounting for at least 25 mass % of the carbon source in the medium while maintaining a pH of 5.0 to 7.0 in the liquid culture from the beginning of the culturing to the end of the culturing of said bacteria.

REFERENCE TO DEPOSITED BIOLOGICAL MATERIAL

The deposition numbers of microorganisms that have been deposited in relation to the present invention are as follows.

(1) *Rhizobium vitis* ARK-1 strain (FERM BP-11426)
(2) *Rhizobium vitis* ARK-2 strain (FERM BP-11427)
(3) *Rhizobium vitis* ARK-3 strain (FERM BP-11428)

The invention claimed is:

1. A method for inhibiting an increase in viscosity of a culture solution of *Rhizobium* bacteria, the method comprising culturing a *Rhizobium* bacterium by liquid culture using a medium comprising one or more carbon sources, wherein a disaccharide accounts for at least 25 mass % of the one or more carbon sources in the medium while maintaining a pH of 5.0 to 7.0 in a culture solution from a beginning of the culturing to an end of the culturing, wherein the disaccharide is at least one selected from the group consisting of maltose, trehalose, and lactose, and
wherein the *Rhizobium* bacterium is a *Rhizobium vitis* ARK-1 strain with accession number FERM BP-11426, a *Rhizobium vitis* ARK-2 strain with accession number FERM BP-11427, a *Rhizobium vitis* ARK-3 strain with accession number FERM BP-11428, or an *Agrobacterium radiobacter* K84 strain.

2. The method of claim 1, wherein the liquid culture is an at least 5-L mass culture.

3. A method for inhibiting an increase in viscosity of a culture solution of *Rhizobium* bacteria and improving viable cell count of the *Rhizobium* bacterium in the culture solution, the method comprising:

culturing a *Rhizobium* bacterium by liquid culture using a medium comprising one or more carbon sources, wherein a disaccharide accounts for at least 25 mass % of the one or more carbon sources in the medium while maintaining a pH of 5.0 to 7.0 in a culture solution from a beginning of the culturing to an end of the culturing; and concentrating and/or separating viable bacteria from the culture solution, wherein the disaccharide is at least one selected from the group consisting of maltose, trehalose, and lactose, and wherein the *Rhizobium* bacterium is a *Rhizobium vitis* ARK-1 strain with accession number FERM BP-11426, a *Rhizobium vitis* ARK-2 strain with accession number FERM BP-11427, a *Rhizobium vitis* ARK-3 strain with accession number FERM BP-11428, or an *Agrobacterium radiobacter* K84 strain.

4. The method of claim 3, further comprising lyophilizing the viable bacteria.

5. The method of claim 3, wherein the liquid culture is an at least 5-L mass culture.

6. The method of claim 1, wherein the viscosity of culture solution is 17 to 44 mPa·s.

7. The method of claim 3, wherein the viable cell count is $2 \times 10^{10}$ to $4.4 \times 10^{10}$ cfu/ml.

8. A method for inhibiting an increase in viscosity of a culture solution of *Rhizobium* bacteria, the method comprising culturing a *Rhizobium* bacterium by aeration-agitation culture using a medium comprising one or more carbon sources, wherein a disaccharide accounts for at least 25 mass % of the one or more carbon sources in the medium while maintaining a pH of 5.0 to 7.0 in a culture solution from a beginning of the culturing to an end of the culturing, wherein the disaccharide is at least one selected from the group consisting of maltose, trehalose, and lactose, and wherein the *Rhizobium* bacterium is a Rhzizobium *vitis* ARK-1 strain with accession number FERM BP-11426, a *Rhizobium vitis* ARK-2 strain with accession number FERM BP-11427, a *Rhizobium vitis* ARK-3 strain with accession number FERMI BP-11428, or an *Agrobacterium radiobacter* K84 strain, whereby, at the time of culturing a *Rhizobium* bacterium, and, at the time of isolating and recovering a viable cell thereof, the viscosity of culture solution of *Rhizobium* bacteria is maintained by inhibiting the increase in viscosity.

\* \* \* \* \*